United States Patent
Micic

(10) Patent No.: US 9,962,717 B1
(45) Date of Patent: May 8, 2018

(54) INSTRUMENT FOR AUTOMATED SAMPLE PREPARATION BY COMBINATION HOMOGENIZATION AND CLARIFICATION

(71) Applicant: MP Biomedicals, LLC, Santa Ana, CA (US)

(72) Inventor: Miodrag Micic, Rancho Santa Margarita, CA (US)

(73) Assignee: MP Biomedicals, LLC, Santa Ana, CA (US)

( * ) Notice: Subject to any disclaimer, the term of this patent is extended or adjusted under 35 U.S.C. 154(b) by 0 days. days.

(21) Appl. No.: 15/665,106

(22) Filed: Jul. 31, 2017

(51) Int. Cl.
| | | |
|---|---|---|
| *B04B 5/10* | (2006.01) | |
| *B01F 11/00* | (2006.01) | |
| *B01F 3/08* | (2006.01) | |
| *B01F 3/20* | (2006.01) | |
| *B04B 1/14* | (2006.01) | |
| *B04B 1/20* | (2006.01) | |
| *B04B 9/10* | (2006.01) | |

(Continued)

(52) U.S. Cl.
CPC .............. *B04B 5/10* (2013.01); *B01F 3/0815* (2013.01); *B01F 3/2071* (2013.01); *B01F 11/0005* (2013.01); *B04B 1/14* (2013.01); *B04B 1/2016* (2013.01); *B04B 9/10* (2013.01); *B04B 15/12* (2013.01); *B01F 11/0028* (2013.01); *B01F 2003/005* (2013.01); *B01F 2003/0849* (2013.01); *B01F 2003/1257* (2013.01); *B04B 9/08* (2013.01); *G01N 1/286* (2013.01); *G01N 2001/2866* (2013.01)

(58) Field of Classification Search
CPC ........... B04B 5/10; B04B 1/14; B04B 1/2016; B04B 15/12; B04B 9/10; B04B 9/08; B01F 11/0005; B01F 3/0815; B01F 3/2071; B01F 2003/1257; B01F 2003/0849; B01F 2003/005; B01F 11/0028; G01N 1/286; G01N 2001/2866

USPC .............................................. 494/20, 47, 84
See application file for complete search history.

(56) References Cited

U.S. PATENT DOCUMENTS

| | | | | |
|---|---|---|---|---|
| 4,078,719 A | * | 3/1978 | Durland .................... | B04B 9/06 188/164 |
| 4,125,335 A | | 11/1978 | Blume et al. | |

(Continued)

FOREIGN PATENT DOCUMENTS

| | | | | |
|---|---|---|---|---|
| EP | 2821146 B1 | * | 5/2016 | ............... B04B 9/10 |

OTHER PUBLICATIONS

FastPrep-24 Classic Instrument. MP Biomedicals, 2017 [retrieved on Oct. 11, 2017]. Retrieved from the internet: <http://www.mpbio.com/product.php?pid=116004500&country=223>.

(Continued)

*Primary Examiner* — Walter D Griffin
*Assistant Examiner* — Shuyi S Liu
(74) *Attorney, Agent, or Firm* — Knobbe Martens Olson & Bear LLP

(57) ABSTRACT

Disclosed herein are instruments and methods for performing both sample homogenization and sample clarification by centrifugation with a single instrument without transferring the sample to a new sample container and without removing or repositioning the sample container within the instrument. In some embodiments, the instrument may automatically perform centrifugation after homogenization. In other embodiments, the instrument may perform both homogenization and centrifugation simultaneously.

23 Claims, 13 Drawing Sheets

(51) Int. Cl.
*B04B 15/12* (2006.01)
*B04B 9/08* (2006.01)
*G01N 1/28* (2006.01)
*B01F 3/12* (2006.01)
*B01F 3/00* (2006.01)

(56) References Cited

U.S. PATENT DOCUMENTS

| | | | |
|---|---|---|---|
| 5,567,050 | A | 10/1996 | Zlobinsky et al. |
| 5,921,477 | A | 7/1999 | Tomes et al. |
| 6,309,875 | B1* | 10/2001 | Gordon .................... B04B 5/02 422/50 |
| 6,579,002 | B1 | 6/2003 | Bartick et al. |
| 6,837,843 | B2* | 1/2005 | Gazeau ................ B04B 5/0421 366/214 |
| 9,759,638 | B1 | 9/2017 | Kido |
| 2013/0042704 | A1* | 2/2013 | Van Duyne ............... B04B 9/08 73/864.91 |
| 2013/0078149 | A1* | 3/2013 | Holmes ................ B04B 5/0414 422/72 |
| 2015/0005150 | A1* | 1/2015 | Meles ...................... B04B 9/10 494/9 |
| 2016/0121278 | A1* | 5/2016 | Hancock ............. B01F 11/0005 366/215 |
| 2016/0368003 | A1* | 12/2016 | Vester ................... B04B 5/0421 |

OTHER PUBLICATIONS

FastPrep 96 Operations Manual. MP Biomedicals, 2011 [retrieved on Oct. 11, 2017]. Retrieved from the Internet: <https://www.mpbio.com/pdf/fastprep/User%20Manuals/FP%20User%20v8.pdf>.

SpeedMill Plus: Powerful and High Efficient Homogenizer. Analytik Jena AG, Jul., 2017. [retrieved on Oct. 11, 2017]. Retrieved from the Internet: <https://www.analytik-jena.de/fileadmin/content/import/imported_dam/14-07-17_SpeedMill_PLUS_eng_WEB_geschuetzt.pdf>.

2010 Geno/Grinder. SPEX SamplePrep, 2014. [retrieved on Oct. 11, 2017]. Retrieved from the Internet: <https://www.spexsampleprep.com/uploads/files/brochures/2010GenoGrinder_Brochure_2014.pdf>.

* cited by examiner

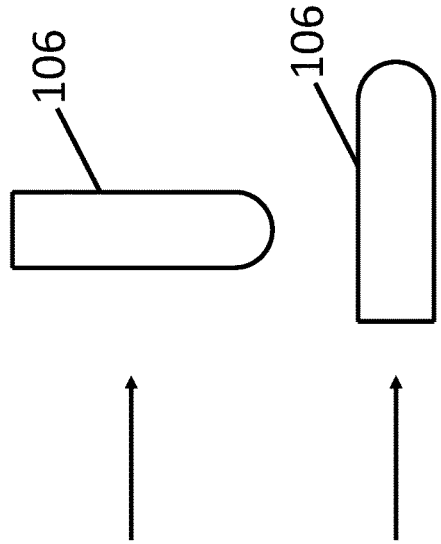
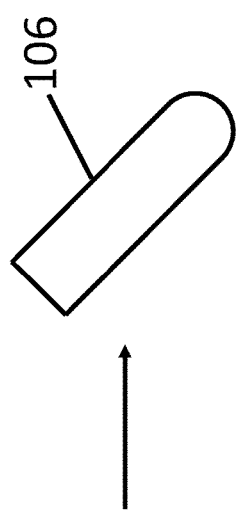
Fig. 2A
Fig. 2B
Fig. 2C

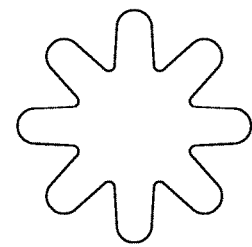
Fig. 5D
Fig. 5E
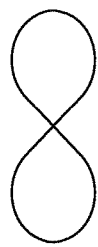
Fig. 5A
Fig. 5B
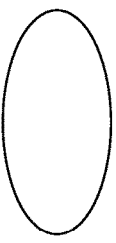
Fig. 5C

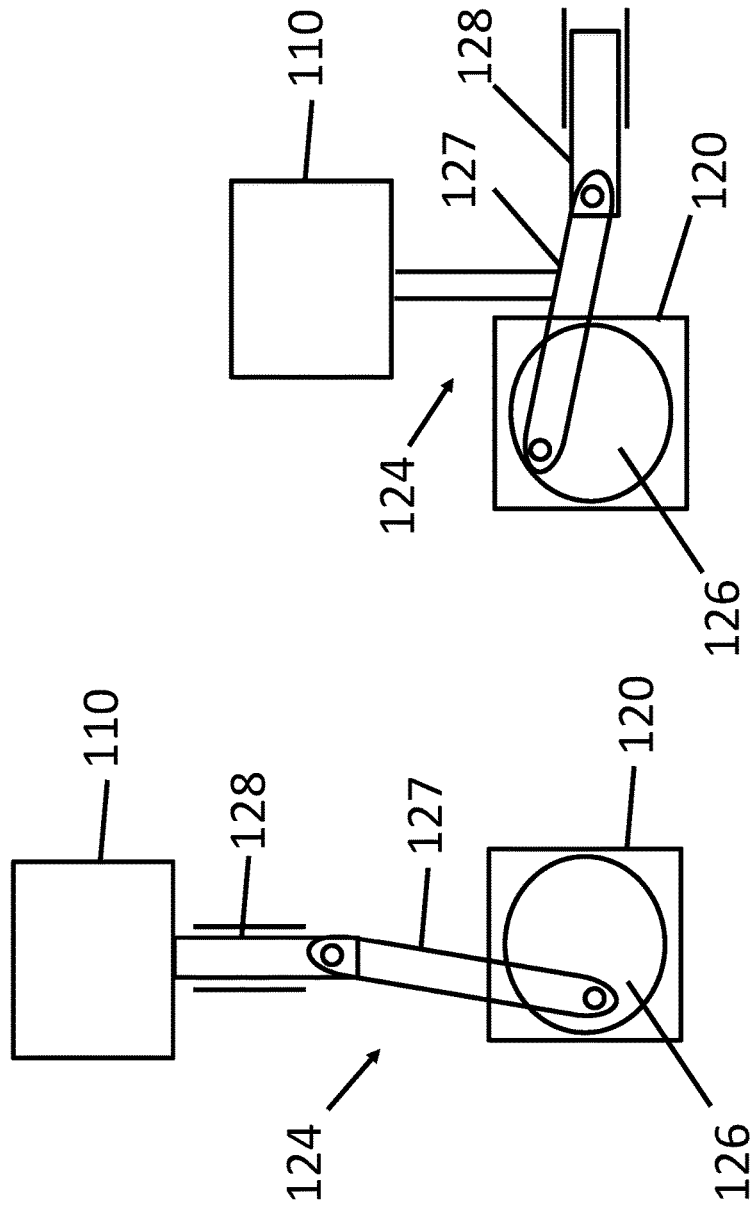

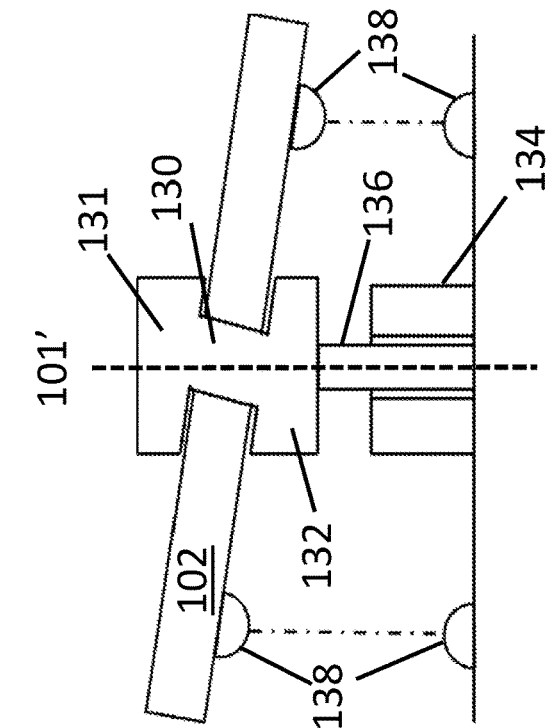
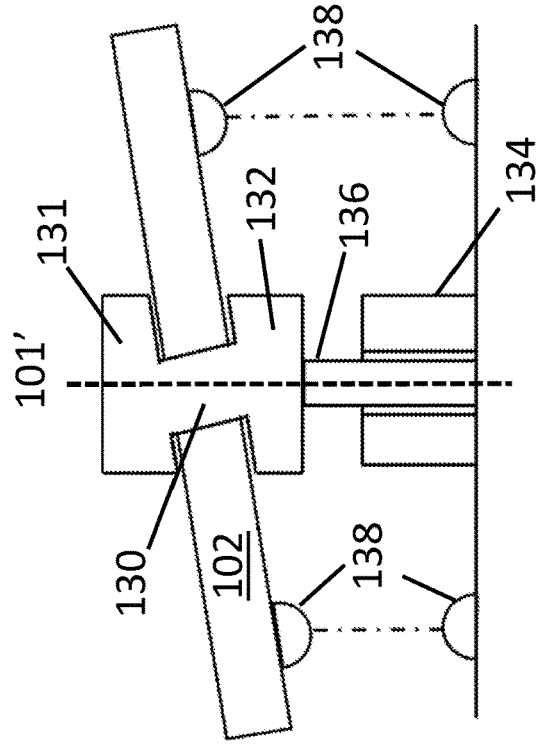

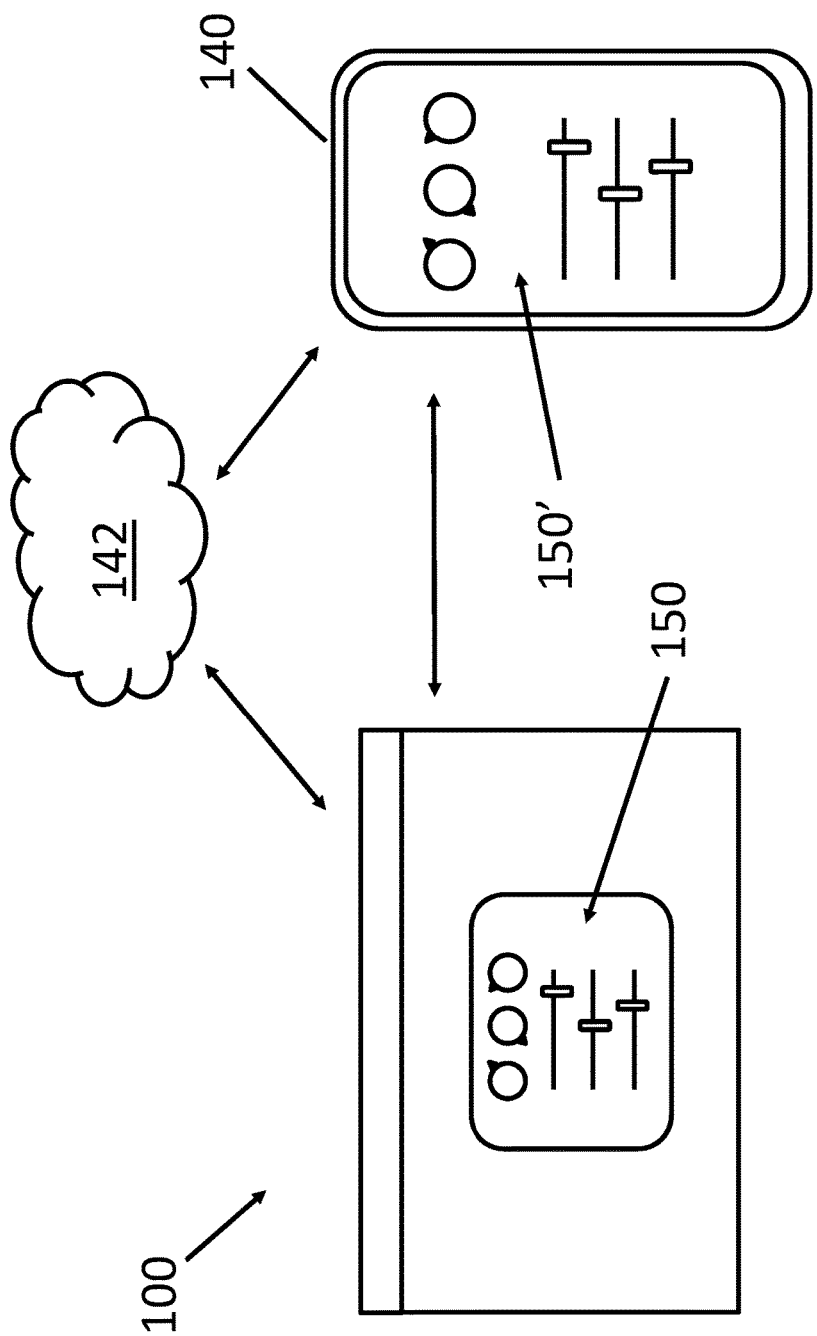

INSTRUMENT FOR AUTOMATED SAMPLE PREPARATION BY COMBINATION HOMOGENIZATION AND CLARIFICATION

BACKGROUND

In biological and chemical solid sample preparation, the bottleneck process is often the process of sample disintegration, which starts with sample milling/grinding, homogenization, and lysis. For instance, often biological molecules of interest are contained within cells, which requires cell lysis to free the molecules of interest into a component of a sample so that it may be further processed (e.g., purified). Usually the process continues by sample clarification, wherein after the sample is processed in some form of mill or homogenizer, and following homogenization and lysis, it is transferred to either a centrifuge or vacuum filtration station for clarification/separation. During centrifugation or vacuum filtration, liquid and solid fractions are separated, and usually the liquid fraction is further used for further purification of molecules of interest. Generally, the sample needs to change its container between the homogenization and separation steps. The transfer may result in a reduced yield of the molecules of interest (e.g., due to adhesion to the sample containers) and/or a dilution of the sample if the sample containers are washed to improve yield. Even if the samples are held in the same containers, many times by moving containers from one machine or station to another, the samples can become mispositioned and/or mislabeled/misidentified. Furthermore, transfer ads another time-wasting step to already bottlenecked process.

SUMMARY

There is a need in the art of sample preparation to have a means for a single step process, with a single piece of equipment and single vial, which accomplish both sample milling/grinding/homogenization/lysis and sample clarification/solid and liquid phase separation, without process interruption and without operator influence. Furthermore, with the increase of scarcity of available lab bench space, it would be beneficial to replace the two instruments commonly employed for lysis/homogenization and centrifugation with one single instruments to perform both functions. This disclosure describes systems, devices, and methods for combined sample lysis/homogenization and centrifugation, particularly for use in laboratory sample preparation, especially in the biological and chemical sciences. The device disclosed herein provides a clear lysate using automated sample grinding, homogenization and lysis of materials, particularly samples of biological and or geological origin, followed by a centrifugation step to clarify the supernatant from solid phase, wherein both operations are performed within the same sample container and instrument. The lysis/homogenization may be accomplished using conventional bead beating techniques.

In some embodiments, an instrument for homogenizing and clarifying a sample contained within a sample container is disclosed. The instrument includes a rotor, an oscillator, and a torque source. The rotor is configured to rotate around a centrifugal axis and has a sample holder configured for reversibly receiving the sample container. The oscillator is configured to reciprocate the rotor along a periodic trajectory at frequencies sufficient to homogenize the sample. The torque source is configured to rotate the rotor around the centrifugal axis at speeds sufficient to clarify the homogenized sample into solid and liquid fractions.

The rotor may be operatively coupled to the torque source by a shaft aligned along the centrifugal axis. The rotor may be removably coupled to the shaft. The rotor may have a plurality of sample holders positioned uniformly around a circumference defined by a radius from the centrifugal axis. In some embodiments, a first plurality of sample holders may be positioned uniformly around a first circumference defined by a first radius from the centrifugal axis and a second plurality of sample holders may be positioned uniformly around a second circumference defined by a second radius from the centrifugal axis. The sample holder can be integral with the rotor. In some embodiments, the sample holder may be vertical, horizontal, or at a fixed angle between 0 and 90 degrees with the centrifugal axis. The sample holder may be configured to swing out during centrifugation. The sample holder can be removable from the rotor. The sample holder can be configured to reversibly receive a plurality of sample containers.

In some embodiments, the periodic trajectory may be linear, elliptical, sinusoidal, a figure-8, and/or nutational. The periodic trajectory may be one-dimensional, two-dimensional, or three-dimensional. In some embodiments, the torque source may be the oscillator. In some embodiments, the oscillator is pneumatically actuated, hydraulically actuated, and/or electromagnetically actuated.

In some embodiments, the torque source can be operatively coupled between the oscillator and the rotor such that the oscillator is configured to reciprocate the torque source and the rotor. In some embodiments, the oscillator can be operatively coupled between the torque source and the rotor such that the torque source is configured to rotate the oscillator and the rotor. In some embodiments, the torque source can be operatively coupled between multiple oscillators. One of the oscillators may be coupled between the torque source and the rotor. In some embodiments, the torque source may be configured to serve as an oscillator as well as a torque source (to rotate and/or shake the rotor).

The oscillator may include a crank slider mechanism, the crank slider having a disc or cylinder configured to rotate about an axis of rotation, a piston configured to linearly reciprocate, and a connecting arm coupling the piston to the disc. The connecting arm can be coupled to the disc at a point set a distance from the axis of rotation. In some embodiments, the rotor may be mechanically coupled to the piston such that the rotor is configured to reciprocate along a linear trajectory. In some embodiments, the rotor is mechanically coupled to the connecting arm such that the rotor is configured to reciprocate along an elliptical trajectory.

The oscillator may have an axis of rotation and include an eccentric shaft extending through the rotor eccentric to the axis of rotation, wherein rotation of the eccentric shaft around the axis of rotation of the oscillator is configured to oscillate the rotor. The oscillation of the rotor may include reciprocally tilting the rotor. The instrument further comprises a first anchoring element positioned on the rotor and a second anchoring element fixed to a non-moving portion of the instrument. The first anchoring element and the second anchoring element may interact to prevent the rotor from continually rotating with the eccentric shaft during reciprocation of the rotor. The first and second anchoring elements can be magnets of opposite polarity, wherein one or both of the magnets is an electromagnet configured to be deactivated during rotation of the rotor around the centrifugal axis such that the rotor is free to rotate. The first and second anchoring elements can be mechanical elements configured to engage one another and configured to disengage during rotation of the rotor around the centrifugal axis such that the rotor is free to rotate. The torque source may be positioned within the eccentric shaft. The torque source may be positioned concentrically outside of the rotor.

The instrument may further include a chamber configured to enclose the rotor and a lid configured to close off the chamber. In some embodiments, the lid can be electromagnetically locked during operation of the instrument. The chamber may be temperature controlled.

The instrument may be configured to actively cool the sample. The rotor may include rotary vanes for forcing airflow over the sample container to cool the sample. The rotor may include one or more Peltier cooling elements for thermoelectrically cooling the sample, the one or more cooling elements being positioned proximate to the sample holder. The one or more cooling elements can be supplied with electrical power through a rotary ring contact. The instrument may further include a refrigeration coil wrapped around the outside or inside of the rotor and connected to a refrigeration unit. The instrument may be configured to introduce cooled air into the chamber enclosing the rotor. The rotor may include internal heat conduction channels. The heat conduction channels may be configured to be flushed with a cooling fluid. The instrument may be configured to passively cool the sample. The rotor may comprise a tray configured to hold dry ice in contact with the sample container for maintaining the sample at low temperature.

The rotor can be configured to rotate at speeds between about 500 rpm and about 15,000 rpm. The rotor can be configured to rotate at speeds between about 500 RCF and about 15,000 RCF. The oscillator can be configured to reciprocate the rotor at speeds between about 4 m/s and about 10 m/s. The oscillator can be configured to reciprocate the rotor at speeds between about 1,000 rpm and about 3,000 rpm. The oscillator can be configured to reciprocate the rotor at about 150 rpm.

The instrument may further include a control panel for setting operating parameters. The control panel can be configured to set speeds and run times for homogenization and centrifugation. 47. The instrument can be configured to allow homogenization only, centrifugation only, or homogenization automatically followed by centrifugation. The instrument may be configured to be controlled by a remote user interface having a processor and memory. The remote user interface can be configured to wirelessly communicate with the instrument. The remote user interface may include a virtual control panel having widgets for setting operation parameters. The remote user interfaces may be configured to store preprogrammed operation parameters. The remote user interface and/or the instrument may be configured to communicate with a remote server.

The instrument may further include the sample container. The sample container may include grinding beads configured to homogenize the sample upon reciprocation of the sample container. The grinding beads may comprise metal, ceramic, glass, or polymer.

In some embodiments, a method for processing a sample within a sample container is disclosed. The method includes placing the sample container within a sample holder of an instrument, wherein the instrument is configured to both homogenize and clarify the sample in a single step without transferring the sample or removing the sample container from the sample holder. The instrument includes a rotor, an oscillator, and a torque source. The rotor is configured to rotate around a centrifugal axis and includes the sample holder positioned at a radial distance from the centrifugal axis. The sample holder is configured for reversibly receiving the sample container. The oscillator is configured to reciprocate the rotor along a periodic trajectory at frequencies sufficient to homogenize the sample. The torque source is configured to rotate the rotor around the centrifugal axis at speeds sufficient to clarify the homogenized sample into solid and liquid fractions. The method further includes using the instrument to homogenize the sample by reciprocating the rotor along the periodic trajectory and using the instrument to clarify the homogenized sample by rotating the rotor around the centrifugal axis at speeds sufficient to separate solid and liquid fractions.

The sample may be a biological sample. The sample may include plant material. The sample may include seed material. The sample may include cells, wherein the homogenization of the sample lyses the cells. The sample may include bacterial cells. The sample may be a geological sample.

The instrument may include a lid which is automatically electromagnetically locked during the homogenization and clarification. The method may include adding bead beating media comprising grinding beads to the sample container prior to placing the sample container within the instrument. The grinding beads may comprise metal, ceramic, glass, polymer, or plastic. The sample holder can be integral with the rotor and placing the sample container within the sample holder can include removing the rotor from the instrument, placing the sample container within the sample holder, and returning the rotor to the instrument. Removing the rotor from the instrument can include releasing the rotor from the instrument and returning the rotor to the instrument can include securing the rotor to the instrument. Releasing the rotor from the instrument and securing the rotor to the instrument can include turning a securing screw.

In some implementations, using the instrument to homogenize the sample can include oscillating the sample between about 4 m/s and about 10 m/s. Using the instrument to homogenize the sample can include oscillating the sample between about 1,000 rpm and about 3,000 rpm. Using the instrument to homogenize the sample can include oscillating the sample at about 150 rpm. Using the instrument to clarify the homogenized sample can include rotating the rotor between about 500 rpm and about 15,000 rpm. Using the instrument to clarify the homogenized sample can include rotating the rotor between about 500 RCF and about 15,000 RCF. The sample may be reciprocated for a duration between about 5 seconds and about 180 seconds. The sample may be reciprocated for a duration between about 20 seconds and about 60 seconds. The sample may be rotated for a duration between about 5 seconds and about 600 seconds. The sample may be rotated for a duration between about 60 seconds and about 300 seconds. The instrument may include a chamber enclosing the rotor, which can be cooled so that the homogenization and clarification are conducted below room temperature. The rotor may be actively cooled. The rotor may be passively cooled.

The homogenization and clarification may be performed automatically upon selection of a program by a user. The homogenization run time and speed and the clarification run time and speed can be set remotely by a user using a remote user interface. In some implementations, the periodic trajectory is linear, elliptical, sinusoidal, a figure-8, and/or nutational. The periodic trajectory may be one-dimensional, two-dimensional, or three-dimensional.

In some implementations, nucleic acids can be isolated in the liquid fraction during clarification. In some implementations, proteins can be isolated in the liquid fraction during clarification.

BRIEF DESCRIPTION OF THE DRAWINGS

FIGS. 2A-2C schematically illustrate various examples of sample container orientation relative to the centrifugal axis.

FIGS. 5A-5E schematically illustrates various examples of trajectories of the shaking motion or alternatively of two-dimensional projections of three-dimensional trajectories.

FIG. 6A shows an example of a torque source operatively positioned between the mechanical oscillator and the rotor. FIG. 6B shows an example of a mechanical oscillator operatively positioned between the torque source and the rotor.

FIGS. 7A-7B schematically illustrate examples of embodiments which use a crank slider for mechanical oscillation.

FIGS. 8A-8D schematically illustrate examples of embodiments which uses eccentric shaft nutation to impart a reciprocal shaking motion on the rotor. FIGS. 8A and 8B schematically illustrate oscillation of the rotor. FIGS. 8C and 8D schematically illustrate centrifugation of the rotor.

FIG. 11 schematically illustrates an example of a system for remote operation of the lyserfuge.

DETAILED DESCRIPTION

Disclosed herein are systems, devices, and methods for performing dual operations on one or more samples using a single instrument, while each sample remains contained within a single sample container. The single instrument may be referred to herein as a lyserfuge. The lyserfuge can be configured to perform both lysis/shaking operations and spinning/centrifugation operations on one or more sample containers. The shaking operation may be configured to grind, homogenize, and/or lyse the sample. The centrifuging operation may be configured to clarify the sample (e.g., separate physical and liquid components). The operations may be performed sequentially (e.g., the shaking followed by the centrifugation) without having to transfer the sample to a new sample container and/or without having to move the sample container to a separate instrument or to a new location within the lyserfuge. In some embodiments, the operations may be performed simultaneously.

Figure 1:
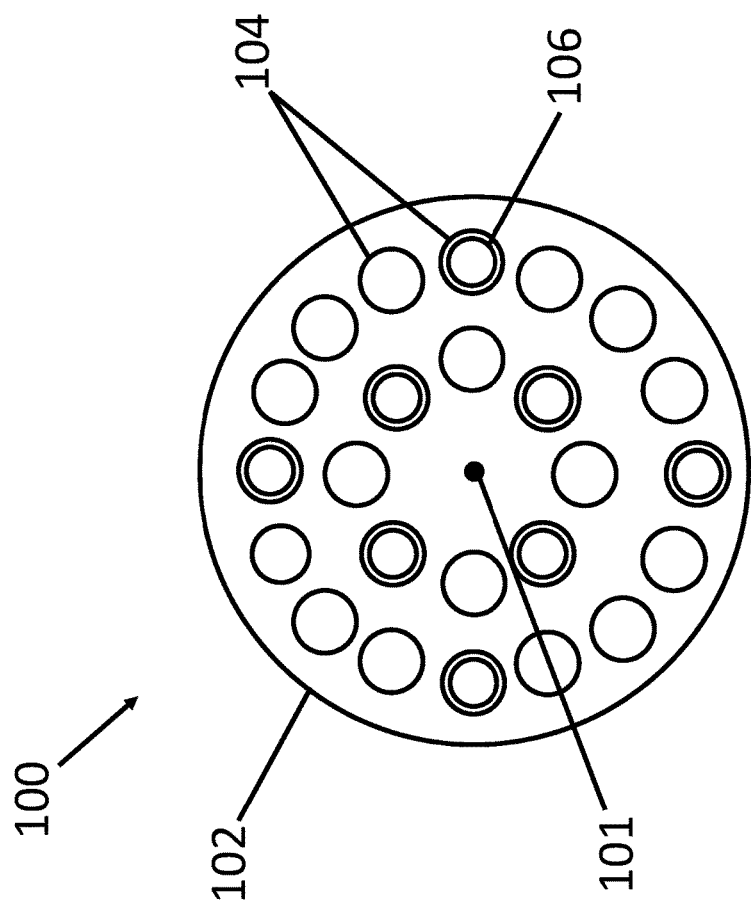
FIG. 1 schematically depicts several components of an example of a lyserfuge.

FIG. 1 schematically depicts several components of an example of a lyserfuge 100. The lyserfuge 100 may comprise a rotor 102 configured for rotation around a centrifugal axis 101. The rotor 102 may comprise sample holders 104 positioned at one or more radii from the centrifugal axis 101 around the rotor 102. The sample holders 104 may be configured to hold sample containers 106 which contain the sample to be homogenized and/or centrifuged. There may be a plurality of sample holders 104 (e.g., two, three, four, five, ten, twenty, thirty, etc., including any integers between two and thirty). In some embodiments, there may be more than thirty sample holders. The sample holders 104 may be uniformly distributed around one or more circumferences of the rotor 102 defined by the one or more radii such that rotor is balanced around any axis of symmetry. The sample holders 104 may be identical or there may be sample holders 104 of different sizes or configurations. In some embodiments, the rotor 102 comprises sample holders 104 positioned at multiple circumferences. For example, there may be two circumferential rows of sample holders 104 with one row being positioned closer to the centrifugal axis 101 and the other row being positioned further from the centrifugal axis 101, as shown in FIG. 1. In some embodiments, there may be more than two rows of sample holders 104. In some embodiments, there may be multiple rows of sample holders 104 positioned vertically above/below each other. In some implementations, multiple rotors 102 may be vertically stacked on one another around the same centrifugal axis 101. They vertically stacked rotors 102 may be integral with one another or separable from one another. In some embodiments, the sample holders 104 may be integral with rotor 102. For example, the sample holders 104 may be recesses (e.g., cylindrical slots) within the rotor 102 configured to receive sample containers 106.

Figure 3:
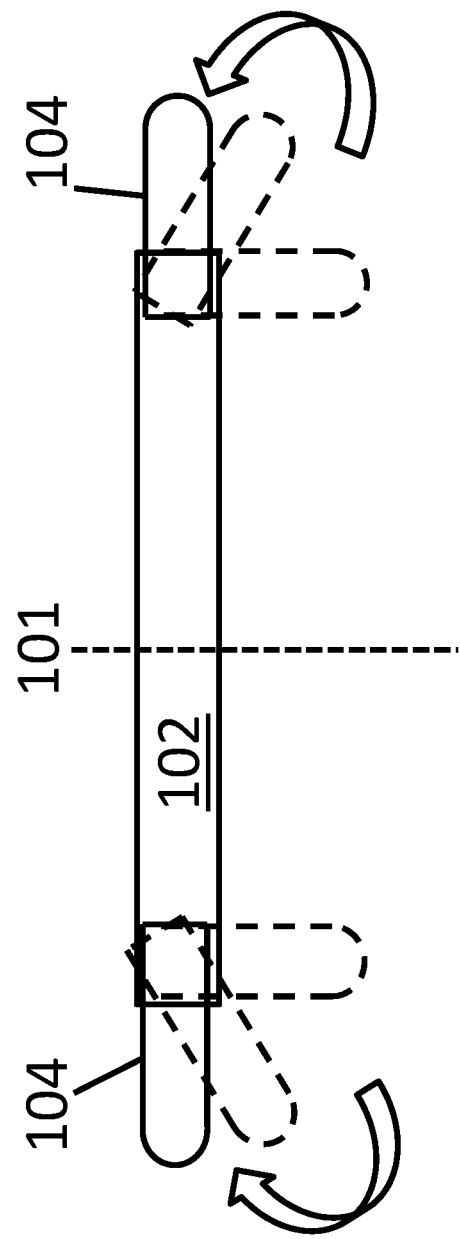
FIG. 3 schematically illustrates a rotor with swing out sample holders.

FIGS. 2A-2C schematically illustrate various examples of sample container 106 orientation relative to the centrifugal axis 101 (the arrows indicate the direction of the centrifugal force which is perpendicular to the centrifugal axis 101). As shown, the sample holders 104 may be configured to orient the sample containers 106 vertically with respect to the centrifugal axis 101 with the top of the sample container 106 pointed upward (FIG. 2A), horizontally with respect to the centrifugal axis 101 with the top of the sample container 106 pointed inward (FIG. 2B), or at a fixed angle there between (i.e. between 0 and 90 degrees with respect to the centrifugal axis 101) (FIG. 2C). In some embodiments, the sample holders 104 may be distinct components from the rotor 102 which are able to be coupled to the rotor 102. In some embodiments, the sample holders 104 may be of a swing-out configuration in which the sample holder 104 is pivotally coupled to the rotor 102 and assumes an operative angle relative to the centrifugal axis 101 upon centrifugation. FIG. 3 schematically illustrates a rotor 102 with swing out sample holders 104. For instance, the sample holder 104 may be a bucket. The sample holders 104 may be removable from the rotor 102. The rotor 102 may be configured to accept sample holders 104 of various sizes and configurations. The rotor 102 may comprise slots for receiving sample holders 104. Each slot may be configured to accept sample holders 104 of various sizes and configurations. In some embodiments, each sample holder 104 holds one sample container 106. In some embodiments, each sample holder 104 may be configured to hold more than one sample container 106.

The sample containers 106 may be standard laboratory containers. The sample containers 106 may be disposable containers configured for one-use applications. For instance, the sample container 106 may comprise disposable plastic (e.g., polystyrene, polyethylene, polycarbonate, etc.). The sample containers 106 may be configured to contain samples of various volumes. For example, the sample containers 106 may hold 0.5 mL, 1.5 mL, 5 mL, 10 mL, 15 mL, 50 mL, 100 mL, 250 mL, etc. In some embodiments, the sample containers 106 may hold any volume less than about 500 mL. In some embodiments, the sample containers may hold volumes greater than or equal to about 500 mL. The sample holders 104 may be configured to hold sample containers 106 of various shapes. The sample containers 106, for example, may be standard laboratory conical tubes, microcentrifuge tubes, multi-well plates, culture flasks, test tubes, laboratory jugs, etc.

Figure 4:
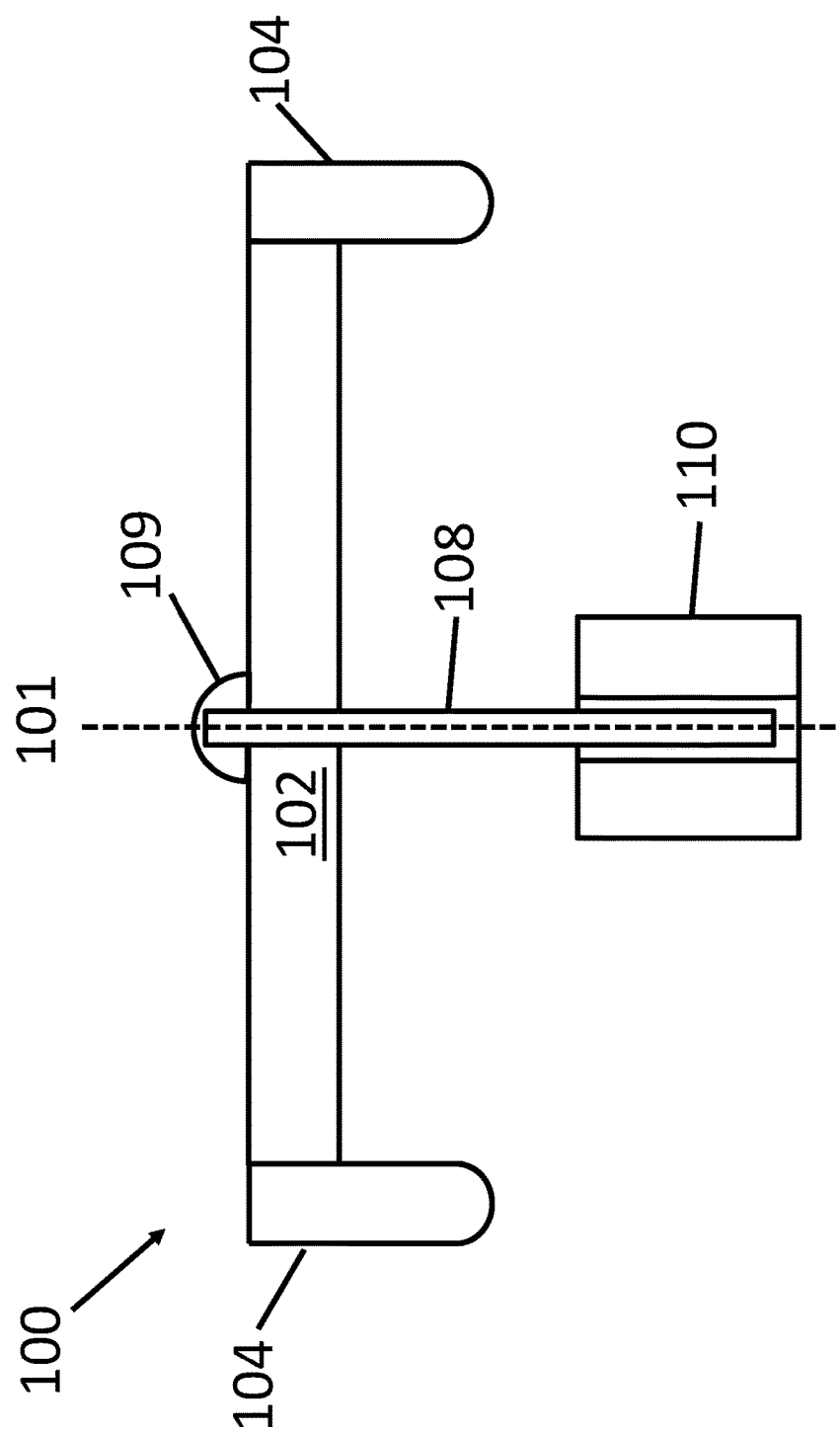
FIG. 4 schematically illustrates an example of a lyserfuge.

FIG. 4 schematically illustrates an example of the lyserfuge 100. The rotor 102 may be configured for rotation around a shaft 108 aligned with the centrifugal axis 101. In some embodiments, the rotor 102 may be removeable from the shaft 108 and the lyserfuge 100. The rotor 102 may removably secured to the shaft 108 by a securing mechanism. The securing mechanism may comprise a cap 109 which attaches to the top of the shaft 108 to secure the rotor 102 to the shaft. For example, the cap 109 may be a threaded cap which screws to the top of the shaft 108 and/or the cap 109 may comprise a push-button release to detach form the shaft 108. Any attachment means known in the art for releaseably securing a rotor to the shaft may be employed. The shaft 108 may be configured to couple to a variety of different rotors 102. The particular rotor 102 attached to the shaft 108 may be configured to hold different types, amounts, or sizes of sample holders 104 and/or sample containers 106. The removability of the rotor 102 may facilitate convenient loading and unloading of sample holders 104 and/or sample containers 106 from the lyserfuge 100.

The shaft 108 may be coupled to a torque source 110 configured to provide a rotational force to the rotor 104. In some embodiments, the shaft 108 may be a flexible coupling and/or may comprise a constant velocity joint, allowing the formation of an angle in the shaft 108 between the rotor 102 and the torque source 110 while maintaining the ability of the shaft 108 to be rotated by torque source 110. The torque source 110 may apply torque to the shaft 108 by any suitable means known by those of ordinary skill in the art. In some embodiments, the torque source 110 may comprise an electromagnetic or ferromagnetic motor, a hydraulic motor, or a pneumatic motor. For example, the torque source 110 may comprise a stator comprising electromagnetics surrounding the shaft 108. The shaft 108 may comprise magnets that are operatively aligned within an inner diameter of the stator and configured to be driven in a rotational direction by controlled activation of the electromagnets of the stator. The torque source 110 may be directly coupled to the shaft 108 (e.g., a direct drive electrical motor). In some embodiments, the torque source 110 may be indirectly coupled to the shaft (e.g., a belt or chain drive configuration, with a belt between the rotor shaft 108 and a motor drive shaft). In some embodiments, a torque source 110 (e.g., an electromagnetic stator) may be positioned inside the rotor 102, such that the shaft 108 is positioned concentrically outside the torque source 110 and integral with the rotor 102, positioned concentrically outside the torque source 110 and coupled to the rotor 102, or omitted altogether. The stator may be configured to be aligned within an internal diameter of the rotor 102 and the rotor 102 may comprise magnets configured to be rotationally driven by the stator. Rotation of the rotor 102 of the lyserfuge 100 may be configured to be operated according to the modes, methods, and mechanisms of conventional centrifuges known by those of ordinary skill in the art.

The lyserfuge 100 may further be configured to impose a shaking motion on the sample containers 106 held in the sample holders 104 of the rotor 102. The shaking motion may be used to promote sample lysis and/or homogenization. The samples may be lysed and/or homogenized by using bead beating, as described elsewhere herein. The shaking motion may be imparted to the entire rotor 102 by the lyserfuge 100. The shaking motion may be imparted to the shaft 108 by the lyserfuge 100. In some implementations, the shaking motion may be a repetitive or periodic motion. FIGS. 5A-5E schematically illustrates various examples of trajectories of the shaking motion or alternatively of two-dimensional projections of three-dimensional trajectories. For example, the trajectory of the shaking motion may be linear (FIG. 5A), elliptical (FIG. 5B), sinusoidal (FIG. 5C), figure-8 (FIG. 5D), nutational (FIG. 5E), etc. In some implementations, these trajectories may be combined to form more complex trajectories and/or these trajectories may represent a trajectory in one plane of motion that may be combined with a trajectory in another plane of motion to create a three-dimensional trajectory. For instance, the various mechanical oscillators disclosed herein may be combined to produce more complex ranges of motion. In some implementations, the motion may be aperiodic or random. The shaking motion may occur in one plane of dimension, two planes of dimension, or three planes of dimension. Motion comprising two dimensional, or, more so, three dimensional movements may be advantageous in inducing more complex and random motion of grinding beads within the sample container 106 providing for optimal lysis and/or homogenization. The shaking motion may be rapid, violent, and/or vigorous for adequately agitating/disrupting the sample and inducing sample lysis and/or homogenization. In some embodiments, the sample containers 106 may be clamped down within the rotor 102 to better secure the samples within the lyserfuge 100 and to provide additional surface area for transferring the forces of the shaking motion to the sample containers 106, particularly for transferring forces from different directions (e.g., from the top of the sample containers 106). For instance, a securing mechanism for securing the rotor 102 to the shaft 108, described elsewhere herein, may comprise a plate for covering and compressing or clamping the sample containers 106 to the rotor 102.

In some embodiments, the shaking motion may be provided by the torque source 110 such that the centrifugation and shaking of the rotor 102 may be accomplished by the same motor. For example, the torque source 110, as illustrated in FIG. 4, may magnetically reciprocate the shaft 108 across the centrifugal axis 101 in a plane perpendicular to the centrifugal axis 101. The torque source 110 may comprise electromagnets axially spaced along centrifugal axis 101 such that the torque source 110 can magnetically reciprocate the shaft 108 along the direction of the centrifugal axis 101. The torque source 110 may be configured to reciprocate the shaft 108 both axially along the centrifugal axis 101 and in a plane perpendicular to the centrifugal axis 101.

Figure 6A:
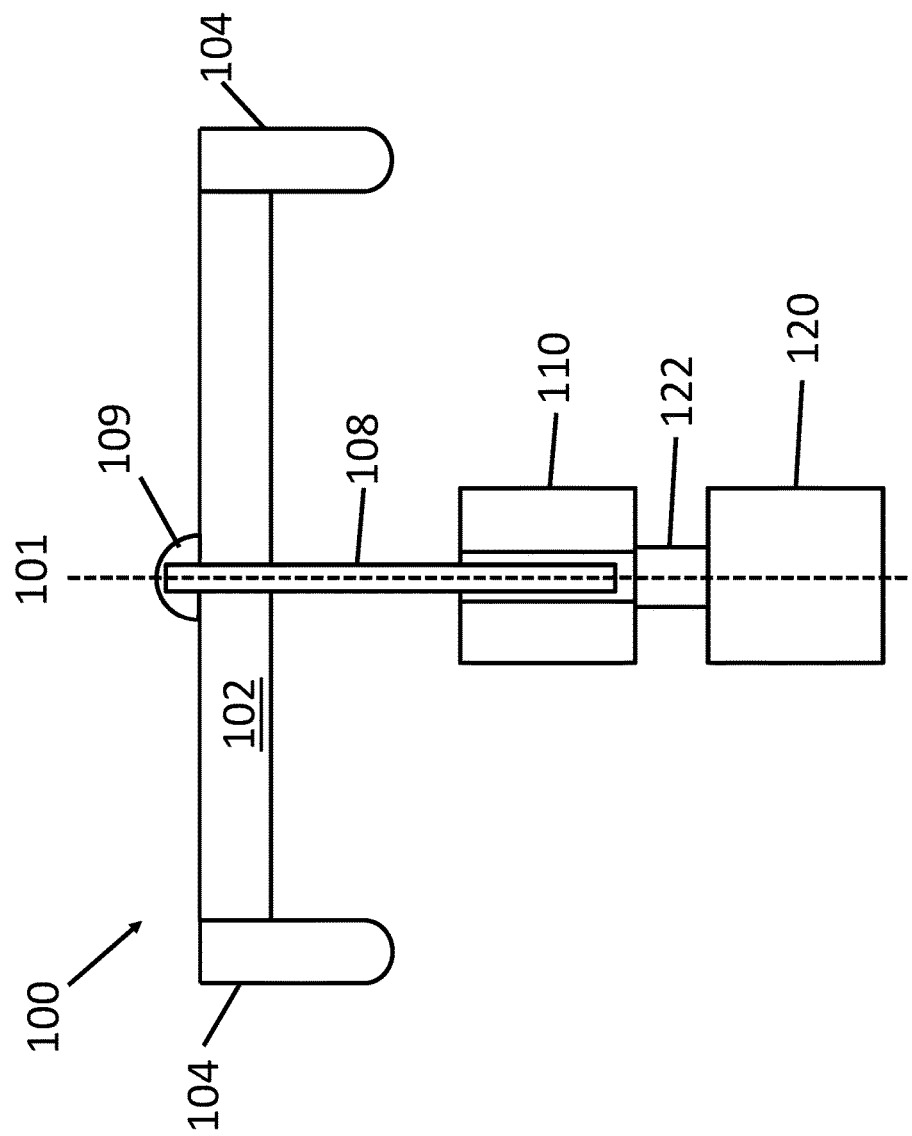
FIGS. 6A-6B schematically depict examples of a lyserfuge.
Figure 6B:
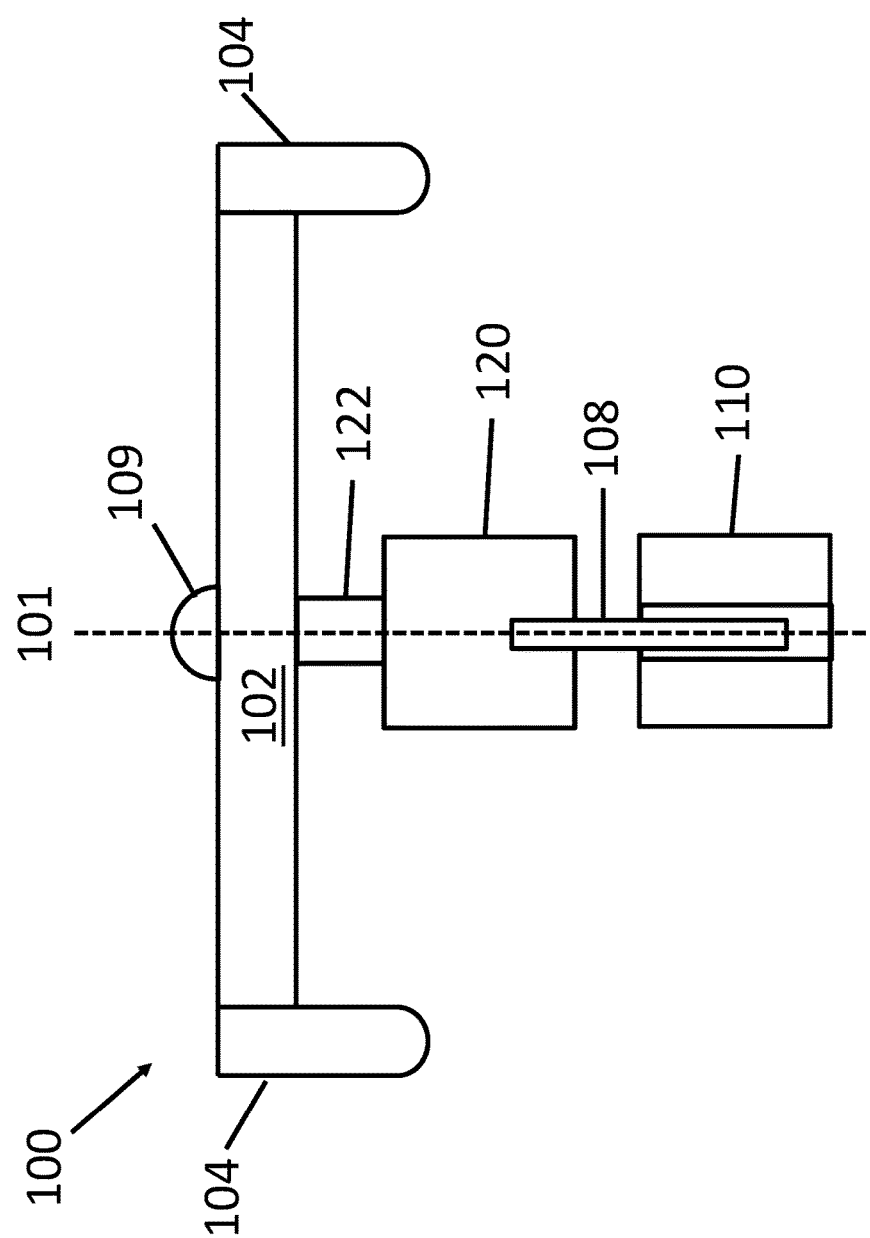

In some embodiments, the shaking motion may be provided by a motor that is separate from that used to provide rotational force for centrifugation (e.g., torque source 110). FIGS. 6A and 6B schematically depict examples of a lyserfuge 100 comprising a rotor 102 coupled to a torque source 110, directly (FIG. 6A) or indirectly (FIG. 6B), by a shaft 108 and further coupled to a mechanical oscillator 120, directly (FIG. 6B) or indirectly (FIG. 6A), by a mechanical connector 122. The mechanical oscillator 120 may comprise a motor for directly generating the oscillatory motion or may be indirectly coupled to a motor. The mechanical connector 122 may be positioned between the torque source 110 and the mechanical oscillator 120 (e.g., the torque source 110 may be positioned above the mechanical oscillator 120) as illustrated in FIG. 6A. In other embodiments, the mechanical oscillator 120 may be positioned between the torque source 110 and the rotor 102, as illustrated in FIG. 6B. In some implementations, the rotor 102 along with the mechanical oscillator 120, coupled together by the mechanical connector 122, may be rotated around the centrifugal axis 101 by torque source 110. The shaft 108 may be rotated by the torque source 110 and coupled to the mechanical oscillator 120 such that the mechanical oscillator rotates together with the shaft 108. The downstream components of the torque source 110 may be configured to be balanced in weight around the shaft 108 so as to facilitate centrifugation.

The mechanical oscillator 120 may apply one-dimensional, two-dimensional, or three-dimensional motion to the rotor 102, sample holders 104, and sample containers 106 (any downstream components of the mechanical oscillator 120) via the mechanical connector 122. In some implementations, the reciprocal motion provided by the mechanical oscillator 120 may be imparted during centrifugation (i.e. simultaneously with the rotational motion imparted by the torque source 110). In some implementations, the reciprocal motion provided by the mechanical oscillator 120 is imparted separately from centrifugation (i.e. before and/or after centrifugation). By way of non-limiting example, the shaking motion imparted by the mechanical oscillator 120 may be provided by electromagnetic, hydraulic, or pneumatic actuators. The torque source 110 and the mechanical oscillator 120 may be permanently coupled or intermittently coupled.

FIGS. 7A and 7B schematically illustrate examples of an embodiment which uses a crank slider 124 for mechanical oscillation. Rotational motion of a rotating disc or cylinder 126 may be converted by the crank slider 124 into a linear reciprocating motion of a piston 128, which is confined to a linear trajectory, by a connecting arm 127. The piston 128 may be coupled directly or indirectly to the rotor 102 such that the reciprocating motion may be imparted to all components downstream of the crank slider 124 (towards the sample container 106). In some embodiments, as shown in FIG. 7A, the linearly reciprocating piston 128 may be coupled directly to the adjacent downstream component (e.g., torque source 110) so that a linear reciprocating motion is imparted to the rotor 102. In other embodiments, as shown in FIG. 7B, the adjacent downstream component may be coupled to the crank slider 124 somewhere along the connecting arm 127, between the piston 128 and the disc 126, such that a two-dimensional elliptical motion is imparted to the rotor 102.

In some embodiments, the mechanical oscillator 120 comprises a magnetic or electromagnetic piston coupled to the adjacent downstream component (e.g., positioned below the torque source 110) and electromagnetically reciprocated in a linear motion (e.g., vertically or horizontally) by an electromagnetic motor to cause the rotor 102 to reciprocate in a linear fashion. In some embodiments, actuation of an electromagnetic piston may be used to actuate a crank slider which is coupled to downstream components. The downstream components may be coupled to the crank slider such that an elliptical reciprocal motion is imparted on the rotor 102, as described elsewhere herein.

Figure 8D:
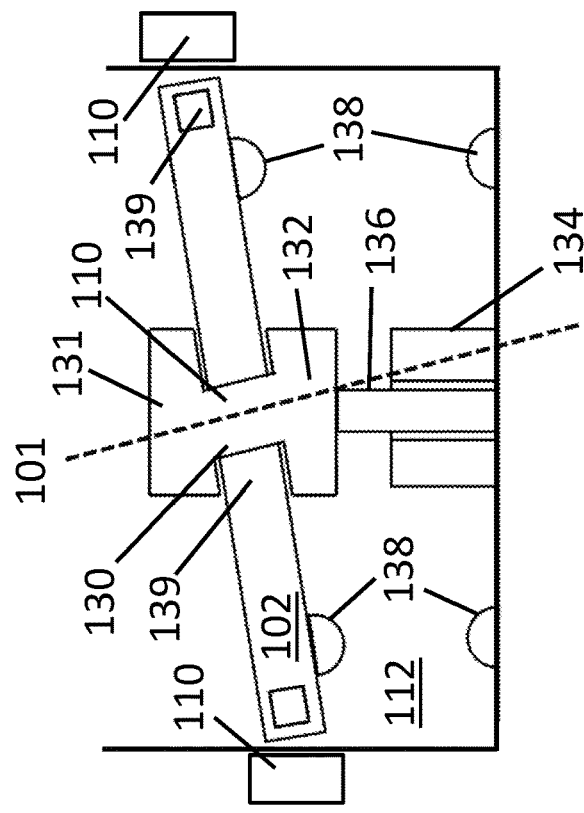

FIGS. 8A-8D schematically illustrates an example of an embodiment which uses eccentric shaft nutation to impart a reciprocal shaking motion on the rotor 102. In some embodiments, the motor is positioned around an eccentric shaft 130. The eccentric shaft 130 may be integral with or coupled to an upper hub 131 and a lower hub 132. In some embodiments, the lower hub 132 may be coupled to the mechanical oscillator 120 by the mechanical connector 122. The mechanical oscillator 120 may be a torque source 134, similar to torque source 110 described elsewhere herein, configured to rotate the mechanical connector 122, which may be a shaft 136, similar to shaft 108 described elsewhere herein. The eccentric shaft 130 may be eccentric to the axis of the shaft 136 (i.e. the axis of eccentric shaft 130 intersects the axis of shaft 136). The shaft 136 may be arranged in a vertical alignment with respect to the lyserfuge 100. The upper hub 131 and/or the lower hub 132 may comprise a surface that transects the axis of the shaft 136 along a plane not perpendicular to the shaft 136. Rotation of the eccentric shaft 130, upper hub 131, and lower hub 132 around the axis of shaft 136 (the axis of rotation 101' of the torque source 134) may cause the rotor 102 to oscillate in a vertical direction. The lyserfuge 100 may comprise bearings between the eccentric shaft 130 and the rotor 102 (e.g., ball bearings). The upper hub 131 and/or the lower hub 132 may be spaced apart from the rotor 102 such that they do not come in contact with the rotor 102. In some embodiments, there may be bearings between the upper hub 131 and the rotor 102 and/or between the lower hub 132 and the rotor 102. The rotation of the eccentric shaft 130 relative to an internal diameter of the rotor 102 through which the eccentric shaft 130 extends may cause may cause the rotor 102 to wobble or tilt as it oscillates such that as one side of the rotor 102 is pushed downward, the opposite side is pushed upward. In some embodiments, the upper hub 131 and/or the lower hub 132 may also come into contact with the rotor (either directly or through a mechanical bearing) and the uneven surface of the hub relative to the axis of rotation 101' of the torque source 134 may facilitate inducement of the mechanical oscillation. FIGS. 8A and 8B schematically illustrate the oscillation of rotor 102 caused by the rotation of shaft 136 by torque source 134. The positioning of rotor 102 in FIG. 8B is the result of rotating the shaft 136 in FIG. 8A by approximately 180 degrees. Upon one complete rotation, the positioning of the rotor 102 may be restored to that illustrated in FIG. 8A.

The lyserfuge 100 may comprise one or more anchoring elements 138 coupled directly or indirectly to the rotor 102 and positioned around the axis of rotation 101'. Each anchoring element 138 on the rotor 102 may be paired with another anchoring element 138 fixed to a non-rotating component or surface of the lyserfuge 100. The anchoring elements 138 of each pair may interact with each other inhibit or prevent the rotor 102 from rotating around the axis of rotation 101' with the eccentric shaft 130. The rotor 102 may be entirely prevented from rotating or may experience a small degree of reciprocation along a circumferential direction (e.g., over a small angle less than 90 degrees). In embodiments comprising a plurality of anchoring elements 138, the anchoring elements 138 may be positioned substantially uniformly around the axis of rotation 101' to provide a relatively even distribution of force to the rotor 102. In some implementations, the anchoring elements 138 may comprise magnets. Each pair of anchoring elements 138 may comprise magnets of opposite polarity which are attracted toward each other. In some implementations, the anchoring elements 138 are mechanically fastened to each other, such as by a spring or elastic band which allows some degree of wobble but which inhibits or prevents rotation. In some implementations, the anchoring elements 138 extend into substantial contact with each other and/or the bottom surface of the anchoring elements 138 on the rotor 102 may extend below the upper surface of the fixed anchoring elements 138.

Figure 8C:
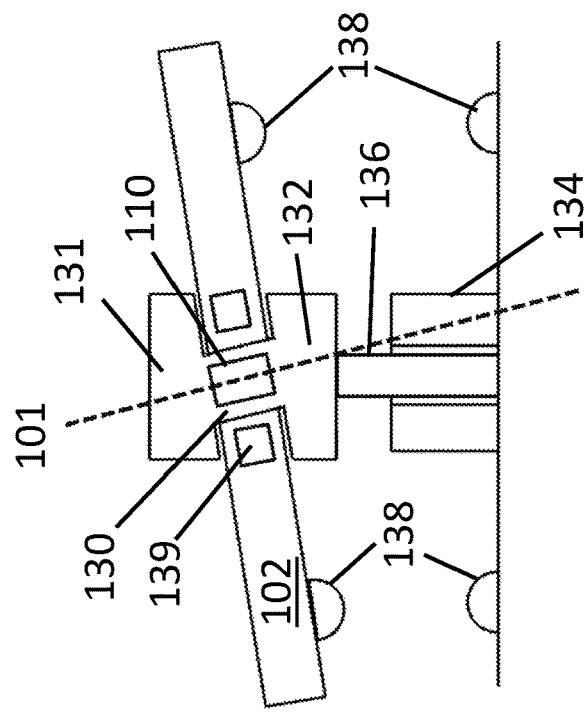

In some embodiments, the rotor 102 is further configured to rotate around the eccentric shaft 130 in a centrifugal mode, as schematically illustrated in FIGS. 8C and 8D. Anchoring elements 138 may be disengaged during centrifugation of rotor 102 such that the rotor 102 is permitted to rotate together with the eccentric shaft 130 around the centrifugal axis 101. For example, the torque source 110 may be positioned concentrically within an inner diameter of the rotor 102, such as within the eccentric shaft 130, as illustrated in FIG. 8C. Rotor magnets 139 positioned within the rotor 102 may be driven by the torque source 110 to cause the rotor 102 to rotate. In some embodiments, the upper hub 131 and lower hub 132 may be configured to releasably secure or grip the rotor 102, such that the rotor 102 is not secured or gripped in the homogenization/shaking mode to allow the eccentric shaft 130 to rotate freely of the rotor 102 and such that the rotor 102 is secured or gripped in the centrifugation mode to allow the rotor 102 to rotate with the eccentric shaft 130. The hubs 131, 132 may releasably secure or grip the rotor using electromagnets and/or a disengageable mechanical mechanism. In some implementations, the hubs 131, 132 may be brought closer together to tightly clamp the rotor between the hubs 131, 132 for centrifugation and/or brought further apart to loosen the rotor 102 for homogenization/shaking. In some embodiments, the torque source 110 may be positioned concentrically outside the outer diameter of the rotor 102 and used to drive rotor magnets 139, as illustrated in FIG. 8D. The torque source 110 may be positioned behind a casing, such as the surface of a chamber 112 within which the rotor 102 is positioned. The eccentric shaft 130 may remain fixed in position and the rotor 102 may rotate freely around the eccentric shaft 130.

In some implementations, the anchoring elements 138 are magnets which are electronically disengaged. For instance, one or both of the magnets of each pair of anchoring elements 138 may be an electromagnet which can be deactivated. In some implementations, the anchoring elements are mechanical elements which can be mechanically disengaged to release the rotor 102 from the securing interaction between the pairs of anchoring elements 138. For instance, the anchoring elements 138 on the rotor 102 may comprise channels into which the fixed anchoring elements 138 extend. During centrifugation, the fixed anchoring elements 138 may be retracted from the channels to allow the rotor 102 to freely rotate. Other suitable means of releasably anchoring the rotor 102 may be employed as well.

In some embodiments, the shaking motion may be imparted by a piezoelectric motor (e.g., a linear inchworm motor) or by activation of one or more piezoelectric crystals. In some implementations, these piezoelectric components may interface the torque source 110, as depicted, for example, in FIG. 6A. In other implementations, these piezoelectric components may interface components downstream of the torque source 110, such as the rotor 102, shaft 108, and/or sample holders 104, as depicted, for example, in FIG. 6B. Piezoelectrics may be particularly useful for imparting relatively small reciprocal motions to the sample container 106 (e.g., on the nanometer scale or micrometer scale). Particularly in cases of small scale vibrations, the piezoelectrics may be able to be coupled downstream of the torque source 110 without interfering with the interfacing of the shaft 108 to the torque source 110. In some embodiments, piezoelectric components may be used to impart ultrasonic vibrations to the sample container 106.

Figure 9:
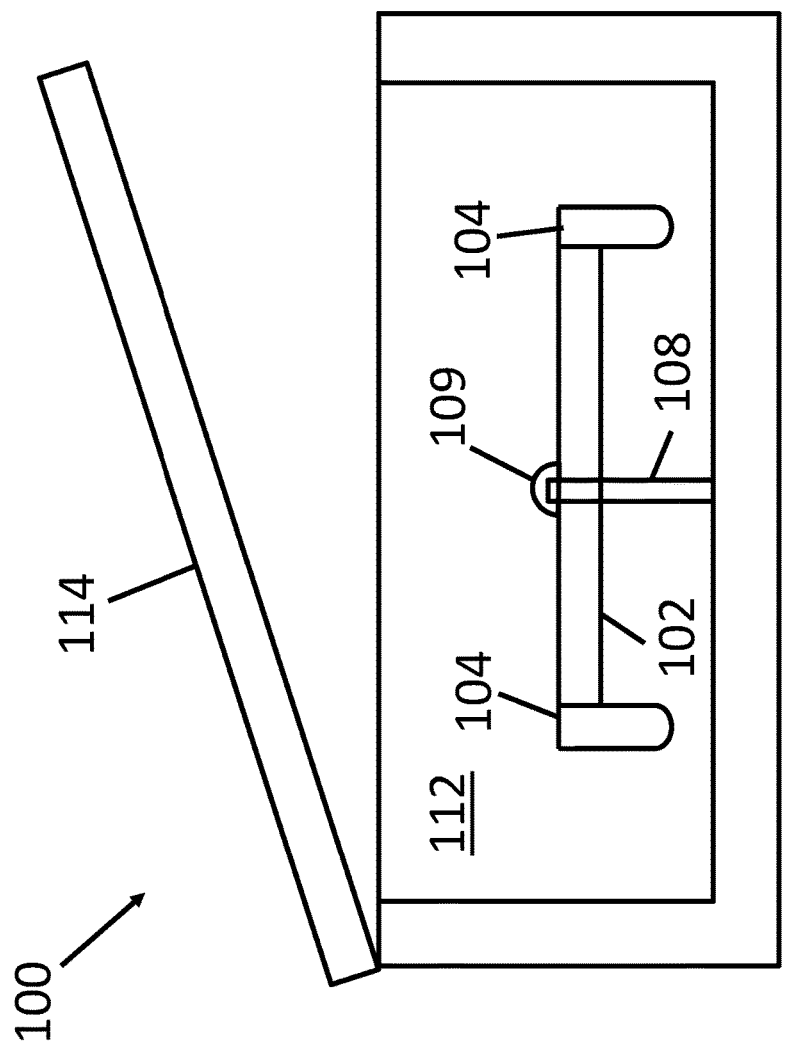
FIG. 9 schematically illustrates an example of a lyserfuge comprising an enclosed rotor.

FIG. 9 schematically illustrates an example of a lyserfuge 100 comprising an enclosed rotor 102. The lyserfuge 100 may comprise a chamber 112 which encloses the rotor 102 and sample holders 104 when being homogenized and/or centrifuged the sample containers 106. The user may access the rotor 102 through the chamber 112 and may load and unload sample containers 106 or the rotor 102, itself, through the chamber 112. The chamber 112 may further enclose the shaft 108, torque source 110, and components responsible for providing shaking motions (e.g., a mechanical oscillator 120 and mechanical connector 122) or portions thereof. Some or all of these components may be inaccessible from the chamber 112. Keeping the mechanical components relatively inaccessible from the user and exterior environment may promote user safety and/or keep the components clean from debris. The chamber 112 may be closed from the exterior environment by a lid 114. The user may open and close the lid 114 to access the chamber 112. The lid 114 may seal the chamber 112 such that it is an insulated environment. The lid 114 may provide a safety feature to the lyserfuge 100 which prevents a user from accessing the chamber 112 during operation of the lyserfuge 100 (e.g., during centrifugation or lysis/homogenization). The lid 114 may have a lock which prevents the user from opening the lid during operation until the mechanical motion has come to a stop or is no longer being actively actuated (e.g., is coasting to a stop). The lyserfuge 100 may magnetically detect whether the lid 114 is in an open or closed position. The lid 114 may automatically lock (e.g., via an electromagnetic latch) once an operation has begun. The motor or motors of the lyserfuge 100 may be locked in a frozen position when the lid 114 is open, such as for loading and unloading of samples.

The lyserfuge 100 may employ passive and/or active cooling to preserve sample integrity during lysis, homogenization, and/or centrifugation operations. The cooling may help to counteract any temperature increases caused by operation of the one or more motors of the lyserfuge 100. For example, in some embodiments the chamber 112 is configured to be cooled. The chamber 112 may be refrigerated. The precise temperature of the chamber 112 may be able to be set by the user, such as by a user interface or digital input. In some embodiments, the rotor 102 may be cooled. In some embodiments, the rotor 102 and the chamber 112 may be cooled. In some embodiments, the rotor 102 and/or the chamber 112 may be heated.

In some embodiments, sample containers 106 can be actively cooled down (e.g., during the lysis process) by use of forced air cooling, Peltier cooling elements (thermoelectric cooling), and/or by refrigeration embedded in the rotor 102. For example, rotary vanes which will direct the airflow may be an integral part of the rotor 102. In another example, one or more Peltier cooling elements may be an integral part of the rotor 102 with cooling sides of the elements being in touch with the sample containers 106, or in a close proximity of the sample holder 104. The Peltier cooling element can be supplied with electrical power through a rotary ring contact. In another example, a refrigeration coil is wrapped around the outside or inside of the rotor 102 and is connected through a central hollow shaft to a refrigerator unit. In another example, air is first cooled down and then forced through the chamber 112 containing the rotor 102. In another example, the rotor 102 may comprise internal heat conduction channels. In some implementations, the heat conduction channels may be flushed with a cooling fluid. The sample can also or alternatively be cooled by passive cooling. For example, the rotor 102 may be made to comprise a tray for holding dry ice. The sample containers 106 can be held in contact with the dry ice or other rapidly evaporating material, maintaining the sample at low temperature.

Figure 10:
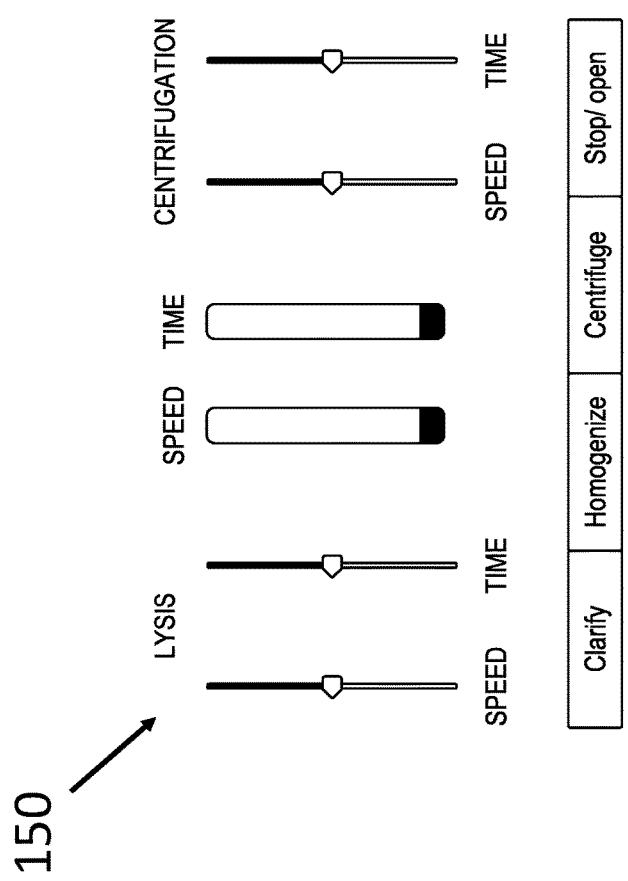
FIG. 10 schematically illustrates an example of a lyserfuge control panel.

The lyserfuge 100 may comprise a control system for controlling and/or monitoring operation of the lyserfuge 100. The control system may include a control panel 150 on which a user can adjust parameters of the lyserfuge 100 operation. In some embodiments, the control panel 150 may be a programmable logic controller (PLC). In some embodiments, the control panel 150 may be comprised of discrete components. FIG. 10 schematically illustrates an example of a control panel 150. The control panel 150 may include controls for setting the speed and run time of the lysis/homogenization and/or centrifugation procedures. In some embodiments, the speed of the shaking motion may be set in units of a linear velocity (e.g., m/s). For example, in some embodiments the shaking speed may be set between about 0.1 m/s and about 50 m/s or ranges there between, between about 1.0 m/s and about 20 m/s, between about 2.0 m/s and 15.0 m/s, between about 4.0 m/s and about 10.0 m/s. The shaking speed may be set in increments (e.g., 1, 2, 3, 4 or 5 m/s). In some embodiments, the shaking may be set in rpm (wherein 1 rpm defines the completion of a single reciprocal motion within 1 minute). For example, in some embodiments the shaking speed may be set between about 10 rpm and about 10,000 rpm or ranges there between, between about 100 rpm and about 5,000 rpm, between about 150 rpm and about 3,000 rpm, between about 500 rpm and about 2,000 rpm, between about 1,000 rpm and about 1,500 rpm. In some embodiments, the shaking may only comprise a single speed operation (e.g., 150 rpm, 1,500 rpm, 2,500 rpm, 3,000 rpm, etc.). In some embodiments, the centrifugation speed may be set in units of rpm and/or G force (xg or RCF). For example, in some embodiments the centrifugation speed may be set between about 100 rpm and between about 50,000 rpm or ranges there between, between about 250 rpm and about 30,000 rpm, between about 500 rpm and about 15,000 rpm. In some embodiments the centrifugation speed may be set between about 100 RCF and between about 50,000 RCF or ranges there between, between about 250 RCF and about 30,000 RCF, between about 500 RCF and about 15,000 RCF. The conversion between the rpm and the G force can depend on the size of the rotor 102 (i.e. the radius from the axis of centrifugation 101 to the sample holder 104). The centrifugation speed may be set in increments (e.g., 500 rpm). In some embodiments, the lysis time may be set between about 5 s and about 60 s, 120 s, 180 s, 240 s, 300 s, or ranges there between. The lysis time may be set in increments. At lower ranges of run time (e.g., 5-60 s), the run time may be set in smaller increments (e.g., 1 s increments). At higher ranges of run time (e.g., 60-180 s), the run time may be set in larger increments (e.g., 15 s increments). In some embodiments, the centrifugation time may be set between about 5 s and about 30 min or ranges therebetween, between about 5 s and about 20 min, between about 5 s and about 15 min, between about 5 s and about 10 min, between about 5 s and about 5 min. At lower ranges of run time (e.g., 5-60 s), the run time may be set in smaller increments (e.g., 1 s increments). At higher ranges of run time (e.g., 1-30 min), the run time may be set in larger increments (e.g., 0.5 min). In some embodiments, there may be a manual actuator (e.g., a button) that performs one of the operations (lysis/homogenization, centrifugation, combined homogenization/centrifugation) for an indefinite period of time while the button is pressed or otherwise activated by the user. In some embodiments, the operation may be set to run indefinitely until stopped by the user. The motor or motors of the lyserfuge 100 may operate with only the standard motor speed controller. A variation of motor speed between about 5% and about 10% may occur. In some embodiments, speed may be monitored by a hall effect sensor/encoder or other suitable sensor.

The control panel 150 may include controls for selecting an operation to run (e.g., lysis/homogenization only, centrifugation only, lysis/homogenization followed by centrifugation, etc.) and/or, where more than one operation is to be performed, for setting an order of operations for the lyserfuge 100 to automatically switch between. In some embodiments, the lyserfuge 100 may be able to perform various types of shaking motions (shaking trajectories). A user may be able to select from the various available motions via the control panel 150. The lyserfuge 100 may include acceleration and/or deceleration levels to choose from (e.g., fast, medium, slow) for the lysis/homogenization and/or the centrifugation. These levels may control the rate of acceleration and/or deceleration between no motion and the speed set by the user. For instance, in some implementations, the centrifugation may be stopped by applying a brake to the rotor. In another implementation the rotor may be slowed down by applying counter-electromagnetic force (counter-EMF) to the stator or rotor. A user may select the level of braking or may select a no brake option, allowing the rotor to more slowly coast to a stop by loss of its own momentum. The control panel 150 may include a stop button which will stop the shaking or rotations in the middle of a run. The stop button may cause a relatively immediate stop (e.g., for emergency stopping) or may cause a gradual stop. In some embodiments, there may be multiple stop buttons inducing stops with different rates of deceleration. In some embodiments, the user may be able to set a temperature of the inner chamber via the control panel 150. There may be controls for opening and/or closing the lyserfuge 100 (e.g., locking and/or unlocking the lid 114).

The control panel 150 may comprise any suitable input controls as are known by those of ordinary skill in the art. For instance, the control panel may comprise, analogue or digital rotary encoders (similar to a conventional volume knob or dial), analogue or digital sliding knobs, level selection buttons, key pads, etc. In some embodiments, the operation parameters may be digitally entered, such as through buttons that allow discrete incrementations between a range of values. The control panel 150 may also comprise notifications, such as display panels, LED indicators, etc. For example, there may be a display of the running time and/or time remaining. There may be a display indicting set speed and/or the current operating speed. The displays may be digital outputs. The displays may be scale bars showing relative progress or absolute times and/or speeds. The control panel 150 may indicate which mode or function the lyserfuge 100 is operating in (e.g., centrifugation, homogenization, etc.). A "cancel" message may be displayed if the operative function was stopped.

FIG. 11 schematically illustrates an example of a system for remote operation of the lyserfuge 100. In some embodiments, the lyserfuge 100 may be operated remotely by an external user interface 140 comprising a processor (e.g., a tablet, smart phone, computer, etc.). The external user interface 140 may store software (e.g., a mobile application) or access software from a remote server 142 to operate the lyserfuge 100. The external user interface 140 may display a virtual control panel 150'. The user may input parameters for operating the lyserfuge 100 via manual entry (e.g., via a keyboard, mouse, touch screen interface, etc.), via voice command, or via any other suitable means known by those of ordinary skill in the art. In some embodiments, the virtual control panel 150' may resemble the physical control panel 150 of the lyserfuge 100, as illustrated in FIG. 11. The virtual control panel 150' may comprise widgets for enabling user input. For example, the virtual control panel 150' may comprise virtual rotary encoders (radio knobs), sliders, incrementers/decrementer, etc. which can be manipulated by a user, such as on a touch screen. The virtual control panel 150' may utilize a virtual keypad for inputting numeric values or alphanumeric parameters. The external user interface 140 may further comprise memory for storing various programs. A user may pre-program a number of operations (e.g., including an order of operations, speeds, run times, etc.) into the external user interface 140 or stored on a remote server 142, such that the user may readily recall the operation parameters and rerun programs. The programs may be stored by custom names or by numbers. For instance, a program labeled "Corn Seed" may store operation parameters for processing certain biological molecules from corn seed samples. In some embodiments, the lyserfuge 100 or associated software or server 142 may comprise common pre-programmed operations for a user to use.

In some embodiments, the lyserfuge 100 may comprise only a physical control panel 150. In other embodiments, the lyserfuge 100 may comprise only a virtual control panel 150'. Still, in other embodiments, the lyserfuge 100 may comprise both a physical control panel 150 and a virtual control panel 150'. In embodiments comprising both physical and virtual control panels 150, 150', the virtual control panel 150' may be automatically updated to reflect adjustments made on the physical control panel 150. The external user interface 140 may be operatively coupled to the lyserfuge 100 via a wireless connection, as illustrated in FIG. 11, (e.g., WiFi, Bluetooth, XBEE, etc.) or a wired connection (e.g., a data cable such as a USB cable). The external user interface 140 and/or the lyserfuge 100 may be in wireless communication with an external server 142 or network of servers such as a cloud network, as described elsewhere herein. In some embodiments, the lyserfuge 100 may comprise a processor and/or memory such that the same operations that are described relative to the external user interface 140 and/or virtual control panel 150' may be performed directly on the lyserfuge 100 (e.g., via control panel 150). For instance, the lyserfuge 100 may comprise an integrated touch-screen which displays a virtual control panel 150' and/or the lyserfuge 100 may comprise memory allowing the storage of a number of programs.

A sample may be processed by the lyserfuge 100 according to any suitable method. In some embodiments, a sample, particularly a sample of biological or geological origin, will be placed in a sample container 106 and combined with bead beating grinding media. The bead beating grinding media may comprise beads that are generally spherical in shape. The beads may comprise glass (e.g., silica), metal (e.g., stainless steel), ceramic (e.g., zirconium oxide), polymer, etc. The beads may range in diameter, for example, between about 100 μm and several mm (e.g., 3 mm). Additional liquids, such as biological buffers or solvents, may be added to the sample container 106. The sample containers 106 may be arranged around the rotor 102 in a symmetrical pattern that balances the weight around the rotor 102, as depicted by way of example in FIG. 1. Balancing the weight of the rotor along all axes of symmetry, as is known in the art, may be advantageous in providing smooth operation of centrifugation procedure, particularly at high speeds. In some implementations, sample containers 106 comprising volumes of non-sample liquids (e.g., water) may be used as balances to balance the rotor 102. The sample containers 106 may first be shook (e.g., rapidly, vigorously, and/or violently shook) until the beads homogenize the sample. The shaking motion causes the beads to rapidly move throughout the sample container 106, agitating and disrupting the solid sample components, including lysing any cells present, to cause homogenization of the sample. In some implementations, the samples may be homogenized in as little as about 20-40 seconds. The homogenized sample, remaining in the sample containers 106, may then be spun/centrifuged until the supernatant and solid phase are separated by centrifugation force. The homogenization and centrifugation may be accomplished using the same rotor 102 as described elsewhere herein. The samples may be cooled during processing to prevent degradation of biological molecules. After centrifugation, the useful fraction of biological molecules, usually contained in the liquid phase, can be transferred out by means of fluid transfer. For example, the supernatant can be decanted from the sample container and subject to further isolation/purification and/or analysis. For instance, the samples may be of biological origin (e.g., cell culture, patient specimens, etc.) and/or geological origin (e.g., plant material or soil containing bacteria). These types of samples may comprise nucleic acids (e.g., DNA, RNA), proteins (e.g., antibodies), viruses, etc. which a user may wish to isolate from other components of the sample. In some instances, the user may wish to isolate the sample for quantitative purposes (e.g., to identify an amount of a molecule of interest within a sample) and/or to scale up the molecule (e.g. to amplify a DNA sequence from the sample using PCR).

In some embodiments, the sample container 106 may be a specialized sample container configured to provide additional sample processing capabilities. For example, the sample container may comprise a filter or other filtration system. The filter may selectively allow passage of molecules of a certain size (e.g., molecular weight) upon certain thresholds of centrifugal force. The sample container 106 may comprise sorbent materials (e.g., beads, porous fillers, surfaces) for adhering molecules of certain types (e.g., DNA sorbent materials). The sample containers 106 may comprise density gradient materials (e.g., gels or fluids) with stepped or progressive density changes. Density gradients may be used to facilitate the separation of molecules based on their mass and size (rate zonal separation) or based on their buoyant density (isopycnic separation). The sample container 106 may comprise microfluidic components for separation of molecules. The force applied during centrifugation may facilitate the migration of different molecules through the microfluidic channels. Any type of centrifugation tube known in the art may be employed by the instrument and methods disclosed herein for providing advanced sample processing. These techniques may be especially useful in separating components of complex samples. For instance, they may facilitate the separation of proteins and nucleic acids upon centrifugation in samples rife with cellular debris and/or other tissue components.

EXAMPLES

Example 1

A sample of 50 mg of fresh leafs of *Arabidoptosis Thaliana* is placed inside a 2 mL plastic tube loaded with lysing matrix A (MP Biomedicals, LLC), and is shaken at 2,500 RPM in a lyserfuge for the total of 60 seconds, together with the lysis buffer from a FastDNA Spin Kit (MP Biomedicals, LLC), during which the complete lysis of the plant leaf tissue occurs. Subsequently, the sample is centrifuged in the lyserfuge in the same 2 mL plastic tube at 14,000 RCF, for a total of 10 minutes to allow complete separation of the solid phase of the homogenized sample from the supernatant. After processing the supernatant via all the steps of the FastDNA kit, a total of 3-30 μg of DNA from the plant is recovered.

Example 2

A 100 mg sample of dry corn kernel is placed into a 2 mL metal lysing matrix tube with lysing matrix A and with additional stainless steel balls and lysing buffer. The sample is shaken at 3,000 RPM in a lyserfuge for 40 seconds, with a lysis buffer from a FastDNA Spin kit, during which the lysis of the sample occurs. Subsequently, the sample is centrifuged without transfer to a different tube in the lyserfuge for 15 minutes at 15,000 RCF to allow quantitative separation of the solid phase of the homogenized sample from the supernatant. After processing the supernatant via all the steps of the FastDNA kit, a total of 15-50 ug of DNA is recovered.

Example 3

The lyserfuge system is also used for processing microbiological and environmental samples as illustrated herein. A 0.8 mL of *E. coli* culture is placed into a lysing matrix B tube (MP Biomedicals, LLC), together lysing buffer from a FastDNA Spin Kit and shaken at 2,000 RPM in a lyserfuge for 40 seconds. Subsequently, the sample is centrifuged in the lyserfuge for 15 minutes at 14,000 RCF. After processing the supernatant via all the steps of the FastDNA kit, a total of 7-10 μg of high quality bacterial DNA is recovered.

All referenced materials/products of the provided examples may be supplied by MP Biomedicals, LLC unless otherwise specified.

It is understood that this disclosure, in many respects, is only illustrative of the numerous alternative device embodiments of the present invention. Changes may be made in the details, particularly in matters of shape, size, material and arrangement of various device components without exceeding the scope of the various embodiments of the invention. Those skilled in the art will appreciate that the exemplary embodiments and descriptions thereof are merely illustrative of the invention as a whole. While several principles of the invention are made clear in the exemplary embodiments described above, those skilled in the art will appreciate that modifications of the structure, arrangement, proportions, elements, materials and methods of use, may be utilized in the practice of the invention, and otherwise, which are particularly adapted to specific environments and operative requirements without departing from the scope of the invention. In addition, while certain features and elements have been described in connection with particular embodiments, those skilled in the art will appreciate that those features and elements can be combined with the other embodiments disclosed herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An instrument for homogenizing and clarifying a sample contained within a sample container, the instrument comprising:
   a rotor configured to rotate around a centrifugal axis, the rotor comprising a sample holder configured for reversibly receiving the sample container;
   a motor configured to rotate the rotor around the centrifugal axis at speeds sufficient to clarify the homogenized sample into solid and liquid fractions; and
   an oscillator configured to reciprocate the rotor in three dimensions along a periodic trajectory at frequencies sufficient to homogenize the sample, wherein the oscillator comprises a crank slider mechanism, the crank slider comprising:
      a disc or cylinder configured to rotate about an axis of rotation;
      a piston configured to linearly reciprocate; and
      a connecting arm coupling the piston to the disc, wherein the connecting arm is coupled to the disc at a point set a distance from the axis of rotation.

2. The instrument of claim 1, wherein the rotor is mechanically coupled to the piston such that the rotor is configured to reciprocate along a linear trajectory.

3. The instrument of claim 1, wherein the rotor is mechanically coupled to the connecting arm such that the rotor is configured to reciprocate along an elliptical trajectory.

4. An instrument for homogenizing and clarifying a sample contained within a sample container, the instrument comprising:
   a rotor configured to rotate around a centrifugal axis, the rotor comprising a sample holder configured for reversibly receiving the sample container;
   a motor configured to rotate the rotor around the centrifugal axis at speeds sufficient to clarify the homogenized sample into solid and liquid fractions; and
   an oscillator configured to reciprocate the rotor in three dimensions along a periodic trajectory at frequencies sufficient to homogenize the sample, wherein the oscillator comprises an axis of rotation and an eccentric shaft extending through the rotor eccentric to the axis of rotation and wherein rotation of the eccentric shaft around the axis of rotation of the oscillator is configured to oscillate the rotor.

5. The instrument of claim 4, wherein the instrument further comprises a first anchoring element positioned on the rotor and a second anchoring element fixed to a non-moving portion of the instrument, and wherein the first anchoring element and the second anchoring element interact to prevent the rotor from continually rotating with the eccentric shaft during reciprocation of the rotor.

6. The instrument of claim 5, wherein the first and second anchoring elements are magnets of opposite polarity and wherein one or both of the magnets is an electromagnet configured to be deactivated during rotation of the rotor around the centrifugal axis such that the rotor is free to rotate.

7. The instrument of claim 4, wherein the instrument is configured to allow homogenization only, centrifugation only, or homogenization automatically followed by centrifugation.

8. The instrument of claim 4, wherein the instrument is configured to be controlled by a remote user interface, the remote user interface comprising a processor and memory.

9. An instrument for homogenizing and clarifying a sample contained within a sample container, the instrument comprising:
   a rotor configured to rotate around a centrifugal axis, the rotor comprising a sample holder configured for reversibly receiving the sample container;

a motor configured to drive the rotation of the rotor around the centrifugal axis at speeds sufficient to clarify the homogenized sample into solid and liquid fractions; and an oscillator configured to reciprocate the motor and the rotor along a periodic trajectory at frequencies sufficient to homogenize the sample, the motor being operatively coupled between the oscillator and the rotor.

10. The instrument of claim 9, wherein the oscillator is configured to reciprocate the rotor in three dimensions.

11. The instrument of claim 9, wherein the instrument is configured to allow homogenization only, centrifugation only, or homogenization automatically followed by centrifugation.

12. The instrument of claim 9, wherein the instrument is configured to be controlled by a remote user interface, the remote user interface comprising a processor and memory.

13. The instrument of claim 9, wherein the oscillator is configured to reciprocate the sample at speeds between about 1,000 rpm and about 3,000 rpm.

14. The instrument of claim 9, wherein motor is configured to rotate the rotor at speeds between about 500 RCF and about 15,000 RCF.

15. The instrument of claim 9, wherein the instrument is configured to automatically homogenize and clarify the sample upon selection of a program by a user.

16. The instrument of claim 1, wherein the motor is operatively coupled between the oscillator and the rotor such that the oscillator is configured to reciprocate the motor and the rotor.

17. The instrument of claim 1, wherein the oscillator is operatively coupled between the motor and the rotor such that the motor is configured to rotate the oscillator and the rotor.

18. The instrument of claim 1, wherein the instrument is configured to allow homogenization only, centrifugation only, or homogenization automatically followed by centrifugation.

19. The instrument of claim 1, wherein the instrument is configured to be controlled by a remote user interface, the remote user interface comprising a processor and memory.

20. The instrument of claim 1, wherein the instrument is configured to automatically homogenize and clarify the sample upon selection of a program by a user.

21. The instrument of claim 4, wherein the motor is operatively coupled between the oscillator and the rotor such that the oscillator is configured to reciprocate the motor and the rotor.

22. The instrument of claim 4, wherein the oscillator is operatively coupled between the motor and the rotor such that the motor is configured to rotate the oscillator and the rotor.

23. The instrument of claim 4, wherein the instrument is configured to automatically homogenize and clarify the sample upon selection of a program by a user.

* * * * *